(12) United States Patent
Chow et al.

(10) Patent No.: US 7,238,645 B1
(45) Date of Patent: Jul. 3, 2007

(54) PESTICIDE FORMULATIONS CONTAINING PHOSPHATE ESTER SURFACTANT AND ALKOXYLATED LIGNOSULFONATE

(75) Inventors: Victor Shui-Chiu Chow, Jamestown, NC (US); Douthitt Pruitt Merritt, Greensboro, NC (US); Lear Michael Haulsee, Marietta, GA (US)

(73) Assignee: Syngenta Crop Protection, Inc., Greensboro, NC (US)

( * ) Notice: Subject to any disclaimer, the term of this patent is extended or adjusted under 35 U.S.C. 154(b) by 379 days.

(21) Appl. No.: 10/381,119

(22) PCT Filed: Sep. 18, 2000

(86) PCT No.: PCT/EP00/09134

§ 371 (c)(1),
(2), (4) Date: Mar. 21, 2003

(87) PCT Pub. No.: WO01/20986

PCT Pub. Date: Mar. 29, 2001

(51) Int. Cl.
*A01N 25/30* (2006.01)
*A01N 51/00* (2006.01)
*A01P 7/04* (2006.01)
*C11D 1/37* (2006.01)

(52) U.S. Cl. ................... 504/358; 514/229.2; 514/772; 514/777; 516/199

(58) Field of Classification Search ................ 504/358; 514/772, 777, 229.2; 516/199
See application file for complete search history.

(56) References Cited

U.S. PATENT DOCUMENTS

| 5,464,807 A | 11/1995 | Claude et al. |
| 5,580,567 A | 12/1996 | Roberts |
| 5,639,711 A | 6/1997 | Kassebaum et al. |
| 6,376,487 B1 * | 4/2002 | Maienfisch et al. ...... 514/229.2 |

FOREIGN PATENT DOCUMENTS

| EP | 0190995 | 8/1986 |
| EP | 0224845 | 6/1987 |
| EP | 0257286 | 3/1988 |
| EP | 0257533 | 3/1988 |
| EP | 0498785 | 8/1992 |
| EP | 0672346 | 9/1995 |
| EP | 0733305 | 9/1996 |
| JP | 60051102 | 3/1985 |
| JP | 61122208 | 6/1986 |
| JP | 04018001 | 1/1992 |
| WO | 95/16351 | 6/1995 |

OTHER PUBLICATIONS

Mohr et al. Plant Physiology. "The Woody Plant Cell", p. 37. Springer. 1995.*

Wyrill et al., "Glyphosate Toxicity to Common Milkweed and Hemp Dogbane as Influenced by Surfactants"; Weed Science, Weed Science Society of America; vol. 25, No. 3; May 1977; pp. 275-287.

* cited by examiner

*Primary Examiner*—S. Mark Clardy
(74) *Attorney, Agent, or Firm*—Rebecca Gegick

(57) ABSTRACT

The present invention relates to a surfactant system for general use in agricultural compositions, including, but not limited to herbicidal, fungicidal and insecticidal formulations comprised of two components: an alkoxylated polyarylphenol phosphate ester surfactant in combination with an alkoxylated lignosulfonate salt surfactant.

15 Claims, No Drawings

PESTICIDE FORMULATIONS CONTAINING PHOSPHATE ESTER SURFACTANT AND ALKOXYLATED LIGNOSULFONATE

FIELD OF THE INVENTION

The present invention relates to a surfactant system for general use in agricultural compositions, including, but not limited to herbicidal, fungicidal and insecticidal formulations comprised of two components: an alkoxylated polyarylphenol phosphate ester surfactant in combination with an alkoxylated lignosulfonate salt surfactant.

BACKGROUND OF THE INVENTION

Alkylphenol ethoxylates (APE's) and their anionic derivatives are surfactants that are well known to industry and have historically been relied upon heavily by agricultural chemical producers. However, formulations containing APEs do not always provide the most desirable combination of design specifications, e.g. product efficacy, working parameters and cost. Traditional non-APE surfactant systems have not been readily adaptable substitutes for APE surfactants. For example, depending on the formulation requirements, calcium dodecylbenzenesulfonate used in conjunction with fatty acid ethoxylates has proven to be an unacceptable APE substitute because of poor performance within one or more design parameters such as emulsion stability, acute toxicity, temporal and thermal stability, chemical and physical stability; solution, suspension or dilution dynamics, and viscosity and suspension stabilization. The inability of industry to adapt existing technology to improve upon characteristics of surfactant systems containing APEs has prompted the development of entirely new line APE surfactants. The additional challenge faced by the scientific community has been to develop new APE surfactants which can be easily made from readily available and cost effective raw materials. Accordingly, there continues to be a need for improved APE surfactants.

SUMMARY OF THE INVENTION

Surprisingly, it has now been discovered that the combination of alkoxylated polyarylphenol phosphate esters (or salts or acid forms thereof) with alkoxylated lignosulfonate salts provides a suitable surfactant system for general us in agricultural products. The surfactant system of the instant invention has been found to provide superior performance in aqueous suspension concentrates of pesticides. The instant invention includes the surfactant composition comprising one or more alkoxylated polyarylphenol phosphate esters (or salts or acid forms thereof) and one or more alkoxylated lignosulfonate salts. The invention also includes the agrochemical formulations containing the instantly disclosed surfactant system. In one embodiment of the invention, the compositions containing the instant surfactant system do not contain or are substantially free of other known APEs. The surfactants of the instant invention are obtained from combining the appropriate alkoxylated polyarylphenol phosphate ester with the appropriate alkoxylated lignosulfonate salt.

The stearic configuration of the polyarylphenol group additionally seems to protect the appropriate alkoxylated polyarylphenol phosphate ester surfactant component of the surfactant system from hydrolytic cleavage typically observed in other known anionic phosphate based surfactant systems.

DETAILED DESCRIPTION OF THE INVENTION

One aspect of the invention is the surfactant system comprising:

a) at least one alkoxylated polyarylphenol phosphate ester of the formula (1):

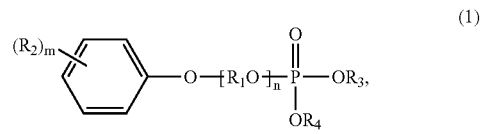

wherein $R_1$ independently is a straight chain or branched $C_2$–$C_4$ alkylene, $R_2$ is phenyl, aryl or alkylaryl, wherein the phenyl nucleus in $R_2$ is unsubstituted or substituted by one to three groups selected from the group consisting of $C_1$–$C_4$ alkyl or $C_1$–$C_4$ alkoxy, and $R_3$ and $R_4$ are independently selected from the group consisting of hydrogen, sodium, potassium, and

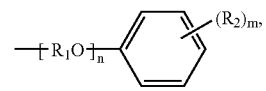

m, is 2 or 3, and n is a number from 1 to 150 inclusive, and b) at least one alkoxylated lignosulfonate salt.

A more preferred embodiment of the invention is the surfactant system, wherein component (a) is the phosphate ester having the formula:

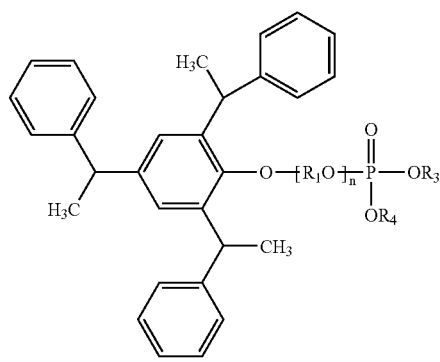

wherein $R_1$ and n are defined as above, and $R_3$ and $R_5$ are independently selected from the group consisting of hydrogen, sodium, potassium, and

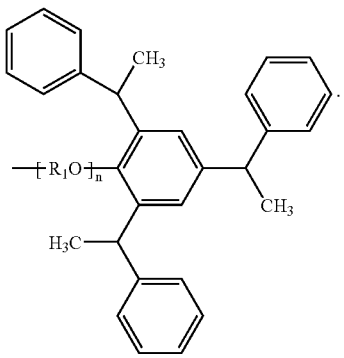

The invention also includes the surfactant system, wherein component (a) is the phosphate ester having the formula:

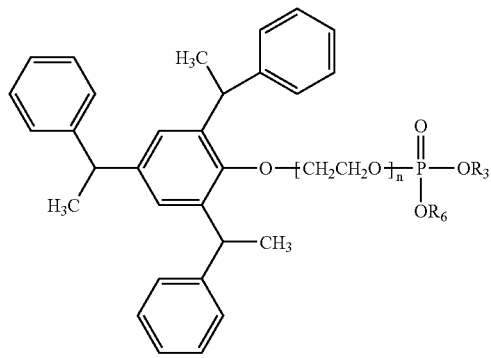

wherein n is defined as above, and $R_3$ and $R_6$ are independently selected from the group consisting of hydrogen, sodium, potassium, and

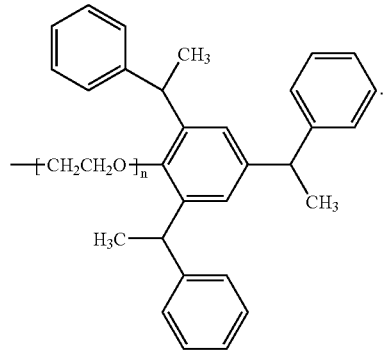

A feature of the invention is where n is 4 to 25, preferably 16. Another aspect of the invention is wherein the surfactant system component (b) is an alkoxylated sulfonated kraft lignin, preferably an ethoxylated sulfonated kraft lignin. A feature of the invention is wherein the surfactant system component (b) is the sodium salt of an ethoxylated sulfonated kraft lignin having an EO equal to 2 to 4, preferably 3.

Another aspect of the invention is the product obtained by the process of combining the components:

a) at least one alkoxylated polyarylphenol phosphate ester of the formula (1):

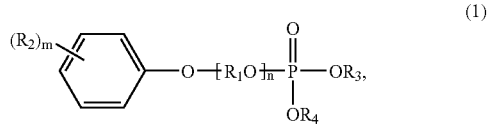

(1)

wherein $R_1$ independently is a straight chain or branched $C_2$–$C_4$ alkylene, $R_2$ is phenyl, aryl or alkylaryl, wherein the phenyl nucleus in $R_2$ is unsubstituted or substituted by one to three groups selected from the group consisting of $C_1$–$C_4$ alkyl or $C_1$–$C_4$ alkoxy, and $R_3$ and $R_4$ are independently selected from the group consisting of hydrogen, sodium, potassium, and

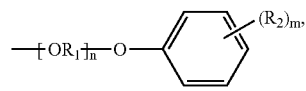

m, is 2 or 3, and n is a number from 1 to 150 inclusive, and b) at least one alkoxylated lignosulfonate salt.

Another aspect of the invention is the product obtained by the process of combining the components:

a) at least one alkoxylated polyarylphenol phosphate ester of the formula (1):

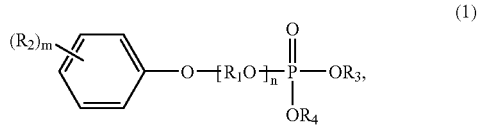

(1)

wherein $R_1$ independently is a straight chain or branched $C_2$–$C_4$ alkylene, $R_2$ is phenyl, aryl or alkylaryl, wherein the phenyl nucleus in $R_2$ is unsubstituted or substituted by one to three groups selected from the group consisting of $C_1$–$C_4$ alkyl or $C_1$–$C_4$ alkoxy, and $R_3$ and $R_4$ are independently selected from the group consisting of hydrogen, sodium, potassium, and

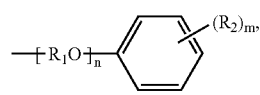

m, is 2 or 3, and n is a number from 1 to 150 inclusive, and b) at least one alkoxylated lignosulfonate salt.

Another aspect of the invention is a chemically integrated surfactant composition comprising:

a) at least one alkoxylated polyarylphenol phosphate ester of the formula (1):

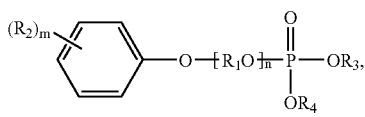

(1)

wherein $R_1$ independently is a straight chain or branched $C_2$–$C_4$ alkylene, $R_2$ is phenyl, aryl or alkylaryl, wherein the phenyl nucleus in $R_2$ is unsubstituted or substituted by one to three groups selected from the group consisting of $C_1$–$C_4$ alkyl or $C_1$–$C_4$ alkoxy, and $R_3$ and $R_4$ are independently selected from the group consisting of hydrogen, sodium, potassium, and

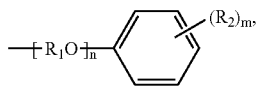

m, is 2 or 3, and n is a number from 1 to 150 inclusive, and b) at least one alkoxylated lignosulfonate salt.

Another aspect of the invention is the pesticide formulation comprising at least one pesticide and a) at least one alkoxylated polyarylphenol phosphate ester of the formula (1):

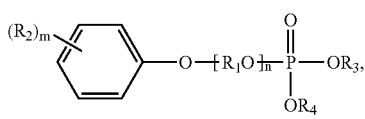

(1)

wherein $R_1$ independently is a straight chain or branched $C_2$–$C_4$ alkylene, $R_2$ is phenyl, aryl or alkylaryl, wherein the phenyl nucleus in $R_2$ is unsubstituted or substituted by one to three groups selected from the group consisting of $C_1$–$C_4$ alkyl or $C_1$–$C_4$ alkoxy, and $R_3$ and $R_4$ are independently selected from the group consisting of hydrogen, sodium, potassium, and

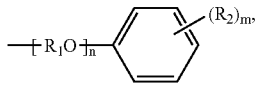

m, is 2 or 3, and n is a number from 1 to 150 inclusive, and b) at least one alkoxylated lignosulfonate salt.

Another feature of the invention is the method of protecting crops comprising the step of applying to the locus of the crops in need of protection an agriculturally effective amount of the one or more of the compositions disclosed herein.

The scope of the invention disclosed herein should not be construed to be limited by any particular chemical theory relating to the complexation, equilibration, reaction or acid-base chemistry of the components used to make the surfactants or other ingredients used to make other ultimately useful formulations (e.g. pesticide formulations). In this regard, another aspect of the invention is the surfactant system comprising one or more alkoxylated polyarylphenol phosphate esters (or salts or acid forms thereof) and one or more alkoxylated lignosulfonate salts wherein the constituent components may or may not have interacted chemically so as to result in a change in form of the components. The invention encompasses the static composition of the appropriate components admixed together as well as the chemically integrated surfactant system composition comprising at least one alkoxylated polyarylphenol phosphate ester and at least one alkoxylated lignosulfonate. "Static composition" denotes the composition composed of components wherein the components have not substantially changed by virtue of their combination with other composition components. "Chemically integrated composition" means a composition that results from the natural equilibration, complexation, dissociation or other chemical transformation if any that may occur after combination of the components and prior to ultimate use of the surfactant system in a pesticide formulation. Therefore, the "chemically integrated composition" of the instant invention by definition encompasses the situation where there is a "static composition" as well as any resultant composition occurring at any point in time between initial creation and ultimate use in the field of products containing the surfactant system. In other words, the disclosed invention is not limited to a static composition of chemically unaltered constituent components.

The invention also includes the method of using the surfactant system as a substitute for known APE surfactants.

Another aspect of the invention is the composition comprising the formulation of the surfactant system disclosed above in pesticide formulations that contain one or more other active ingredients. However, the invention is not limited to pesticide formulations. Other useful formulations that may contain the instantly disclosed surfactant system include shampoo formulations, detergent formulations generally and soap formulations used in the mining industry. The surfactant system presently disclosed is considered to have general applicability as a substitute for known APE surfactants, and therefore would be expected to be useful in many other known formulations. The invention encompasses any formulation obtained by otherwise substituting the instantly disclosed surfactant system for known APEs. The instantly disclosed invention also encompasses any formulation obtained by supplementing compositions containing APEs. Generally, any formulation that conventionally makes use of surfactant additives would be subject to modification by substitution or supplementation with the instantly disclosed surfactant system. Although the surfactant combination herein is disclosed as a surfactant system, it is expected that it will also have other nonsurfactant properties that may be useful independently of any inherent surfactant properties. Depending on the application of the instant invention, it may result in increased bioefficacy and/or reduced toxicity and irritation.

Another aspect of the invention is the composition comprising the formulation of the surfactant system disclosed above in formulations that contain one or more herbicides and one or more safeners (antidotes). When applying herbicides, the cultivated plants may also suffer severe damage owing to factors that include the concentration of the herbicide and the mode of application, the cultivated plant itself, the nature of the soil, and the climatic conditions such as exposure.

The alkoxylated polyarylphenol phosphate esters are either commercially available, prepared by known procedures or otherwise obtained using known chemistry. For example ethoxylated tristyrylphenol phosphate esters may be prepared from the corresponding tristyrylphenol ethoxylate by reaction with phosphorus pentoxide dissolved in phosphoric acid. The tristyrylphenol ethoxylate in turn may be prepared by treating tristyrylphenol with a base (e.g. sodium hydroxide or potassium hydroxide) followed by addition of the desired equivalents of ethylene oxide. Tristyrylphenol is either commercially available, may be prepared by known procedures or otherwise may be prepared using conventional chemistry knowledge. Also mixtures if different phenols (e.g. mixtures of tristyrylphenol and distyrylphenol) may be used as starting materials for preparing the phosphate ester surfactant components of the instant invention.

The alkoxylated lignosulfonates are either commercially available, prepared by known procedures or otherwise obtained using known chemistry. For example, the alkoxylated lignosulfonates may be obtained by alkoxylation of the lignosulfonates using known alkylene oxide reagents, such as ethylene oxide. In particular, the desirable alkoxylated lignosulfonates are those selected from the group consisting of ethoxylated lignosulfonates, propoxylated lignosulfonates and butoxylated lignosulfonates. Other useful alkoxylated lignosulfonates are those compounds resulting from for example mixed alkoxylation whereby the alkylene oxide units introduced vary or alternate for example between ethylene oxide and propylene oxide. The degree of alkoxylation may vary depending on the desired formulation design parameters, e.g. emulsion stability of pesticide formulations.

The lignosulfonates or sulfonated lignins used to make the alkoxylated lignosulfonates are well known in the art, and are for example derived from the sulfite pulping of wood and by sulfonation of lignins derived from the kraft pulping of wood. The lignin materials used are typically in the salt form (i.e. sodium, potassium, etc.). The lignosulfonates which may be utilized for preparing the alkoxylated lignosulfonate surfactants of the instant invention are commercially available, may be obtained from known procedures or otherwise prepared using known chemistry. Typically lignosulfonates may be obtained by sulfonation of spent sulfite liquors from wood conversion. It is preferable to use purified lignosulfonate material in which the sugars and other polysaccharide constituents have been removed and/or destroyed, or additionally inorganic constituents have been partially or fully eliminated.

The alkoxylated lignosulfonates used to make the surfactant system of the invention are preferably those compounds that are readily available and inexpensive. However, cost of materials is only one factor in selecting the alkoxylated lignosulfonates starting materials. After performing a routine cost-benefit analysis and in view of other design parameters it may become apparent that more expensive and less readily available starting materials may be preferred.

Typically the degree of alkoxylation in the alkoxylated polyarylphenol phosphate ester and in the alkoxylated lignosulfonate is independently measured in terms of the average number of alkylene oxide units therein. The "average number of ethylene oxide units" is designated as an "EO" number. Similarly, the average number of propylene oxide and butylene oxide units is designated as a "PO" and "BO" number, respectively. "Average" is defined as the arithmetic mean of a set of real numbers. A preferred feature of the invention is where there is a continuous and symmetrical bell curve population distribution around the EO, PO or BO number. The alkoxylated surfactant components of the invention may contain mixtures of different alkoxy units, e.g. EO+PO+BO. It is also desirable that there below dispersion preferably within one standard deviation (a) of the mean (average EO).

TABLE

Degree of alkoxylation in the surfactant system components.

| | Alkoxylated polyarylphenol phosphate ester | | | Alkoxylated lignosulfonate | | |
|---|---|---|---|---|---|---|
| | EO | PO | BO | EO | PO | BO |
| Preferably | 1 to 150 | 1 to 100 | 1 to 50 | 1 to 12 | 1 to 6 | 1 to 3 |
| More preferably | 4 to 25 | 2 to 20 | 1 to 10 | 1 to 4 | 1 to 3 | 1 to 2 |
| Most preferably | 16 | 8 | 4 | 3 | 2 | 1 |

By "alkyl" is meant an alkyl group that may be linear or branched. By "aryl" is meant either a non-heteroaromatic ring system or heteroaromatic ring system. By "alkylaryl" is meant an aryl group substituted by one or more alkyl groups, wherein the "aryl" may be either a non-heteroaromatic ring system or heteroaromatic ring system.

By "raft lignin" is meant material typically recovered from alkaline pulping black liquors such as are produced in the kraft, soda and other well known alkaline pulping operations.

By "sulfonated lignin" is meant the product which is obtained by the introduction of sulfonic acid groups into the kraft lignin molecule, as may be accomplished by reaction of the kraft lignin with sulfite or bisulfite compounds, so that the kraft lignin is rendered soluble in water.

By "sulfite lignin" is meant the reaction product of lignin which is obtained during the sulfite pulping of wood, and is a principle constituent of spent sulfite liquor.

By "alkoxylated lignosulfonate" is meant the reaction product obtained by alkoxylating lignosulfonates with an alkylene oxide, such as ethylene oxide.

Another preferred feature of the present invention is the combination of the presently disclosed surfactant system with one or more co-surfactants. The co-surfactants are those compounds known in the art for formulating surfactant systems. The co-surfactants include polyglycol ethers, aliphatic alcohols, cycloaliphatic alcohols, alkylphenols (e.g. nonylphenol), saturated fatty acids, unsaturated fatty acids, polyglycol ether derivatives of aliphatic or cycloaliphatic alcohols, or saturated or unsaturated fatty acids. Said derivatives contain 3 to 30 glycol ether groups and 8 to 20 carbon atoms in the (aliphatic) hydrocarbon moiety. A more preferred co-surfactant is a nonionic co-surfactant, especially the nonionic co-surfactant selected from the group consisting of ethylene glycol and polyethylene glycol. Other preferred surfactants may include, castor oil ethoxylates, tristyrylphenol ethoxylates, ethylene oxide/propylene oxide block copolymers (pluronics), and/or ethylene oxide/propylene oxide block copolymers of aliphatic alcohols.

A preferred aspect of the invention includes the combination of the surfactant system herein with a liquid pesticide composition so as to obtain an emulsifiable concentrate formulation which can be directly mixed with water or other aqueous solution to give an aqueous pesticide formulation without special mixing procedures.

A preferred aspect of the invention includes the combination of the surfactant system herein with a solid pesticide composition so as to obtain a suspension concentrate formulation which can be directly mixed with water or other aqueous solution to give an aqueous pesticide formulation without special mixing procedures.

A preferred aspect of the invention includes the combination of the surfactant system herein with a liquid pesticide composition and solid pesticide composition so as to obtain a suspoemulsion concentrate formulation which can be directly mixed with water or other aqueous solution to give an aqueous pesticide formulation without special mixing procedures.

The following examples illustrate further some of the specific features of the invention but are not intended to limit its scope. Where not otherwise specified throughout this specification and claims, temperatures are given in degrees centigrade.

One preferred feature of the invention includes combining the surfactant system previously described with a liquid active ingredient to obtain an emulsifiable concentrate formulation which can be readily diluted with water or other liquid carriers requiring no special handling or mixing procedures. An example of such a formulation follows:

EXAMPLE 1

An aqueous emulsion concentrate containing Compound A as active ingredient was prepared according to the following formulation (indicated percentages are weight percentages):

47.6% Compound A (see Table),
    4.0% tristyrylphenol ethoxylate phosphate ester (16EO),
    2.0% ethoxylated lignosulfonate (3EO),
    5.0% glycerin,
    0.1% xanthan gum,
    0.1% silicone antifoam,
    0.05% preservative,
    2.0% attapulgite clay, and water to make up 100%.

The above ingredients were formulated as follows: (1) A premix of water, the Compound A, the ethoxylated tristyrylphenol and the ethoxylated lignosulfonate is prepared. (2) The premix from (1) is ground to a fine particle size. (3) The remaining ingredients are added to the premix followed by mixing until uniform composition is obtained.

EXAMPLE 2

An aqueous emulsion concentrate containing Compound A, mefenoxam, fludioxinil and difenoconazole as active ingredient was prepared according to the following formulation (indicated percentages are weight percentages):

20.6% Compound A (see Table 3),
    0.35% mefenoxam,
    0.25% fludioxinil,
    1.3% difenoconazole,
    4.0% tristyrylphenol ethoxylate phosphate ester (16EO),
    2.0% ethoxylated lignosulfonate (3EO),
    0.1% sodium hydroxide (50% aqueous solution)
    0.1% nonylphenol,
    20.0% glycerin,
    10.0% titanium oxide,
    2.5% blue pigment,
    0.75% montmorillonite clay,
    0.13% xanthan gum,
    0.06% preservative, and water to make up 100%.

The above ingredients were formulated as follows: (1) A premix of water, the Compound A, the mefenoxam, the fludioxinil, the difenoconazole, the ethoxylated tristyrylphenol and the ethoxylated lignosulfonate, is prepared. (2) The premix from (1) is ground to a fine particle size. (3) The remaining ingredients are added to the premix followed by mixing until uniform composition is obtained.

The crop protection compositions which are part of the instantly disclosed invention may be formulated in a form suitable for the intended application. Types of formulations include for example a flowable (FL) flowable concentrate for seed treatment (FS), wettable powder (WP), wettable dispersible granules (WDG), oil miscible flowable concentrate (OF), suspension concentrate (SC), emulsifiable concentrate (EC), liquid (L), water in oil emulsions (EW), granules (GR) water dispersible powder for slurry treatment (WS) and dry flowable (DF).

Some additional preferred embodiments of the instant invention are contained in Tables 1 and 2 below.

TABLE 1

Crop protection formulations containing surfactant, specified co-surfactant components and one or more active technical components.

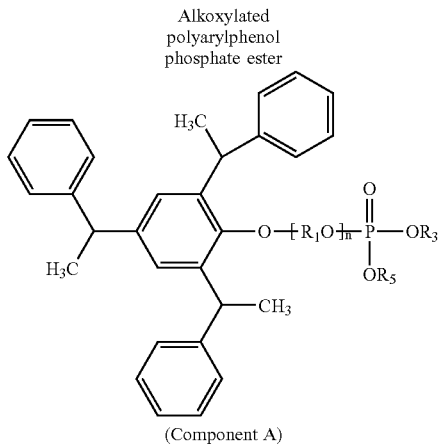

Alkoxylated polyarylphenol phosphate ester (Component A)

| | R₁ | n | Salt | Alkoxylated lignosulfonate salt (Component B) Degree of alkoxylation | Co-surfactant | Active Technical T₁ | Active Technical T₂ | Active Technical T₃ |
|---|---|---|---|---|---|---|---|---|
| 1 | —CH₂CH₂— | 16 | Na | 2 to 4 | Butoxy EO/PO block polymer | metolachlor* | | |
| 2 | —CH₂CH₂— | 16 | Na | 3 | Butoxy EO/PO block polymer | metolachlor* | | |
| 3 | —CH₂CH₂— | 16 | Na | 2 to 4 | EO/PO block polymer | atrazine | | |
| 4 | —CH₂CH₂— | 16 | Na | 2 to 4 | ethylene glycol | atrazine | | |
| 5 | —CH₂CH₂— | 4 to 25 | Na | 2 to 4 | EO/PO block polymer | atrazine | | |
| 6 | —CH₂CH₂— | 4 to 25 | Na | 3 | EO/PO block polymer | atrazine | | |
| 7 | —CH₂CH₂— | 16 | Na | 2 | EO/PO block polymer | atrazine | | |
| 8 | —CH₂CH₂— | 16 | Na | 2 to 4 | Castor oil ethoxylate | atrazine | metolachlor* | |
| 9 | —CH₂CH₂— | 16 | Na | 2 to 4 | Butoxy EO/PO block polymer | atrazine | metolachlor* | |
| 10 | —CH₂CH₂— | 16 | Na | 2 to 4 | Castor oil ethoxylate | flumetralin | | |
| 11 | —CH₂CH₂— | 16 | Na | 2 to 4 | Castor oil ethoxylate | oxasulfuron | | |
| 12 | —CH₂CH₂— | 16 | Na | 2 to 4 | tristyrylphenol ethoxylate | propiconazole | | |
| 13 | —CH₂CH₂— | 16 | Na | 2 to 4 | Butoxy EO/PO block polymer | metribuzin | metolachlor* | |
| 14 | —CH₂CH₂— | 16 | Na | 3 | Butoxy EO/PO block polymer | metribuzin | metolachlor* | |
| 15 | —CH₂CH₂— | 16 | Na | 2 to 4 | Butoxy EO/PO block polymer | flumetsulam | metolachlor* | |
| 16 | —CH₂CH₂— | 16 | Na | 3 | Butoxy EO/PO block polymer | flumetsulam | metolachlor* | |
| 17 | —CH₂CH₂— | 16 | Na | 2 to 4 | Castor oil ethoxylate | flumetsulam | metolachlor* | atrazine |
| 18 | —CH₂CH₂— | 16 | Na | 2 to 4 | Butoxy EO/PO block polymer | flumetsulam | metolachlor* | atrazine |
| 19 | —CH₂CH₂— | 16 | Na | 2 to 4 | Butoxy EO/PO block polymer | mefenoxam | | |
| 20 | —CH₂CH₂— | 16 | Na | 2 to 4 | Butoxy EO/PO block polymer | mefenoxam | fludioxinil | |
| 21 | —CH₂CH₂— | 16 | Na | 2 to 4 | Butoxy EO/PO block polymer | metalaxyl | | |
| 22 | —CH₂CH₂— | 16 | Na | 2 to 4 | Butoxy EO/PO block polymer | metalaxyl | fludioxinil | |
| 23 | —CH₂CH₂— | 4 to 25 | Na | 2 to 4 | Butoxy EO/PO block polymer | diazinon | | |
| 24 | —CH₂CH₂— | 16 | Na | 2 to 4 | Butoxy EO/PO block polymer | diazinon | | |
| 25 | —CH₂CH₂— | 16 | Na | 2 to 4 | Butoxy EO/PO block polymer | dicamba | | |
| 26 | —CH₂CH₂— | 16 | Na | 2 to 4 | Castor oil ethoxylate | dicamba | | |
| 27 | —CH₂CH₂— | 16 | Na | 2 to 4 | nonylphenol | COMPOUND A | | |

TABLE 1-continued

Crop protection formulations containing surfactant, specified co-surfactant components and one or more active technical components.

Alkoxylated polyarylphenol phosphate ester

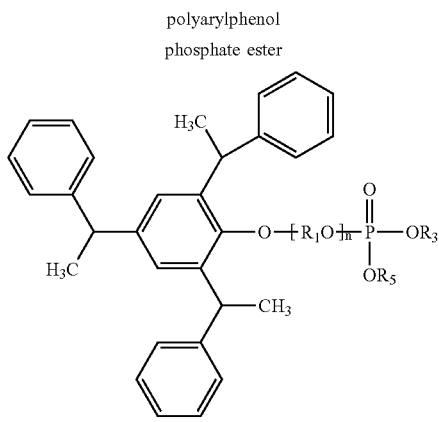

| | (Component A) $R_1$ | n | Salt | Alkoxylated lignosulfonate salt (Component B) Degree of alkoxylation | Co-surfactant | Active Technical $T_1$ | Active Technical $T_2$ | Active Technical $T_3$ |
|---|---|---|---|---|---|---|---|---|
| 28 | —$CH_2CH_2$— | 16 | Na | 2 to 4 | nonylphenol | COMPOUND A | mefenoxam | |
| 29 | —$CH_2CH_2$— | 16 | Na | 2 to 4 | nonylphenol | COMPOUND A | mefenoxam | fludioxinil |
| 30 | —$CH_2CH_2$— | 16 | Na | 2 to 4 | nonylphenol | COMPOUND A | difenoconazole | mefenoxam + fludioxinil |
| 31 | —$CH_2CH_2$— | 16 | Na | 2 to 4 | nonylphenol | COMPOUND A | difenoconazole | |
| 32 | —$CH_2CH_2$— | 16 | Na | 2 to 4 | nonylphenol | COMPOUND A | fludioxinil | |
| 33 | —$CH_2CH_2$— | 16 | Na | 2 to 4 | Castor oil ethoxylate | COMPOUND A | | |
| 34 | —$CH_2CH_2$— | 16 | Na | 2 to 4 | Butoxy EO/PO block polymer | glyphosate or salts | | |
| 35 | —$CH_2CH_2$— | 16 | Na | 2 to 4 | Butoxy EO/PO block polymer | glyphosate isopropylammonium | | |
| 36 | —$CH_2CH_2$— | 16 | Na | 2 to 4 | Butoxy EO/PO block polymer | glyphosate sesquisodium | | |
| 37 | —$CH_2CH_2$— | 16 | Na | 2 to 4 | Butoxy EO/PO block polymer | glyphosate trimesium | | |
| 38 | —$CH_2CH_2$— | 16 | Na | 2 to 4 | Butoxy EO/PO block polymer | fluthiacet-methyl | | |
| 39 | —$CH_2CH_2$— | 16 | Na | 2 to 4 | Butoxy EO/PO block polymer | glyphosate or salts | fluthiacet-methyl | |
| 40 | —$CH_2CH_2$— | 16 | Na | 2 to 4 | Butoxy EO/PO block polymer | glyphosate isopropylammonium | fluthiacet-methyl | |
| 41 | —$CH_2CH_2$— | 16 | Na | 2 to 4 | Butoxy EO/PO block polymer | glyphosate sesquisodium | fluthiacet-methyl | |
| 42 | —$CH_2CH_2$— | 16 | Na | 2 to 4 | Butoxy EO/PO block polymer | glyphosate trimesium | fluthiacet-methyl | |
| 43 | —$CH_2CH_2$— | 16 | Na | 2 to 4 | Butoxy EO/PO block polymer | flumiclorac-pentyl | | |

TABLE 1-continued

Crop protection formulations containing surfactant, specified co-surfactant components and one or more active technical components.

| | (Component A) $R_1$ | n | Alkoxylated lignosulfonate salt (Component B) Salt | Degree of alkoxylation | Co-surfactant | Active Technical $T_1$ | Active Technical $T_2$ | Active Technical $T_3$ |
|---|---|---|---|---|---|---|---|---|
| 44 | —CH$_2$CH$_2$— | 16 | Na | 2 to 4 | Butoxy EO/PO block polymer | glyphosate or salts | flumiclorac-pentyl | |
| 45 | —CH$_2$CH$_2$— | 16 | Na | 2 to 4 | Butoxy EO/PO block polymer | glyphosate isopropylammonium | flumiclorac-pentyl | |
| 46 | —CH$_2$CH$_2$— | 16 | Na | 2 to 4 | Butoxy EO/PO block polymer | glyphosate sesquisodium | flumiclorac-pentyl | |
| 47 | —CH$_2$CH$_2$— | 16 | Na | 2 to 4 | Butoxy EO/PO block polymer | glyphosate trimesium | flumiclorac-pentyl | |
| 48 | —CH$_2$CH$_2$— | 16 | Na | 2 to 4 | Butoxy EO/PO block polymer | glufosinate or salts | | |
| 49 | —CH$_2$CH$_2$— | 16 | Na | 2 to 4 | Butoxy EO/PO block polymer | glufosinate | | |
| 50 | —CH$_2$CH$_2$— | 16 | Na | 2 to 4 | Butoxy EO/PO block polymer | glufosinate ammonium | | |
| 51 | —CH$_2$CH$_2$— | 16 | Na | 2 to 4 | Butoxy EO/PO block polymer | glufosinate or salts | fluthiacet-methyl | |
| 52 | —CH$_2$CH$_2$— | 16 | Na | 2 to 4 | Butoxy EO/PO block polymer | glufosinate | fluthiacet-methyl | |
| 53 | —CH$_2$CH$_2$— | 16 | Na | 2 to 4 | Butoxy EO/PO block polymer | glufosinate ammonium | fluthiacet-methyl | |
| 54 | —CH$_2$CH$_2$— | 16 | Na | 2 to 4 | Butoxy EO/PO block polymer | glufosinate or salts | flumiclorac-pentyl | |
| 55 | —CH$_2$CH$_2$— | 16 | Na | 2 to 4 | Butoxy EO/PO block polymer | glufosinate | flumiclorac-pentyl | |
| 56 | —CH$_2$CH$_2$— | 16 | Na | 2 to 4 | Butoxy EO/PO block polymer | glufosinate ammonium | flumiclorac-pentyl | |
| 57 | —CH$_2$CH$_2$— | 16 | Na | 2 to 4 | Butoxy EO/PO block polymer | glyphosate | atrazine | |
| 58 | —CH$_2$CH$_2$— | 16 | Na | 2 to 4 | Butoxy EO/PO block polymer | glyphosate | metolachlor* | atrazine |
| 59 | —CH$_2$CH$_2$— | 16 | Na | 2 to 4 | Butoxy EO/PO block polymer | glyphosate salt | atrazine | |
| 60 | —CH$_2$CH$_2$— | 16 | Na | 2 to 4 | Butoxy EO/PO block polymer | glyphosate salt | metolachlor* | atrazine |

*includes the racemic mixtures or s-metolachor
Degree of alkoxylation = average number of alkylene oxide units

TABLE 2

Crop protection formulations:

Surfactant system used:

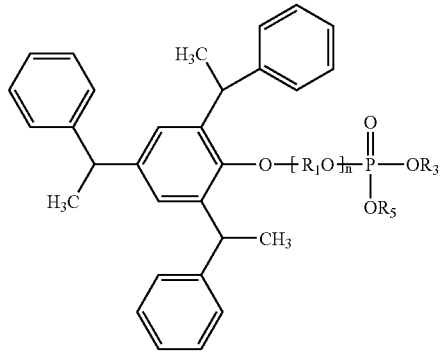

plus Ethoxylated Kraft Lignosulfonate Salt
$R_1$, $R_3$, $R_5$ and n are defined above
Active technical ingredients used and formulation type:

| ACTIVE TECHNICAL $T_1$ | ACTIVE TECHNICAL $T_2$ | ACTIVE TECHNICAL $T_3$ | FORMULATION TYPE |
|---|---|---|---|
| Atrazine | | | FL, WP, WDG, OF |
| Atrazine | Flumetsulam | | FL, WP, WDG, OF |
| Atrazine | Metolachlor | | SC, OF, WDG |
| Atrazine | Flumetsulam | Metolachlor | SC, OF, WDG |
| Ametryn | | | OF, EC, WP, L, WDG |
| Chlorothalonil | | | FL, WDG, WP |
| Chlorothalonil | Metalaxyl | | EC, WDG, WP, OF |
| Cyprodinil | | | EC, WP, OF, WDG |
| Cyromazine | | | WP, L |
| Diazinon | | | EW, W, EC, WDG |
| Dicamba | | | GR, L |
| Dicamba | Prosulfuron | | WDG |
| Difenoconazole | | | WP, EC, WS, FS |
| Difenoconazole | Metalaxyl | | WP, EC, WS, FS |
| Diofenolan | | | EC, WP |
| Fenoxycarb | | | WP, WDG, EC |
| Fenoxycarb | Pymetrozine | | WP, WDG, EC |
| Fludioxinil | | | L, FS, WDG, WP |
| Fludioxinil | Mefenoxam | | L, FS, WDG, WP |
| Fludioxinil | Metalaxyl | | L, FS, WDG, WP |
| Fludioxinil | Propiconazole | | L, FS, WDG, WP |
| Flumetralin | | | EC, WDG, WP |
| Flumetralin | Oxasulfuron | | EC, WDG, WP |
| Flumetsulam | | | EC, WDG, WP, OF |
| Flumetsulam | Metolachlor | | EC, WDG, WP, OF |
| Fluometuron | | | L, DF, WP |
| Fluthiacet-methyl | | | EC, WDG, WP |
| Fluthiacet-methyl | Glyphosate | | EC, WDG, WP |
| Fluthiacet-methyl | Oxasulfuron | | EC, WDG, WP |
| Isazofos | | | EC, GR |
| Mancozeb | | | SC, FL, WDG, WP |
| Mancozeb | Metalaxyl | | SC, FL, WDG, WP |
| Mefenoxam | | | EC, WP, GR, FL, L |
| Metalaxyl | | | EC, GR, L, WP |
| Methidathion | | | EC, WP |
| Metolachlor | | | EC, DF, GR |
| Metolachlor | Metribuzin | | WDG, OF, EC |
| Metolachlor | Simazine | | WDG, OF, SC |
| s-Metolachlor | | | EC, DF, GR |
| s-Metolachlor | Metribuzin | | WDG, OF, EC |
| s-Metolachlor | Simazine | | WDG, OF, SC |
| Metribuzin | | | EC, DF, WDG, OF |
| Norflurazon | | | DE, GR |
| Primisulfuron | | | WDG, WP |
| Primisulfuron | Prosulfuron | | WDG, WP |
| Profenofos | | | EC |
| Prometon | | | EC, FL, OF, WP |
| Prometryn | | | WP, L, OF |
| Propiconazole | | | EC, WP |
| Pymetrozine | | | WDG, WP |
| Simazine | | | WP, WDG, L, GR |
| Triforine | | | WP, EC |
| Trinexapac-ethyl | | | EC, WDG, |
| COMPOUND A | | | WDG, OF, EC, SC |
| COMPOUND A | Difenoconazole | | WDG, OF, EC, SC |
| COMPOUND A | | Fludioxinil | WDG, OF, EC, SC |
| COMPOUND A | Difenoconazole | Fludioxinil | WDG, OF, EC, SC |
| COMPOUND A | Mefenoxam | | WDG, OF, EC, SC |
| COMPOUND A | Difenoconazole | Mefenoxam | WDG, OF, EC, SC |
| COMPOUND A | Fludioxinil | Mefenoxam | WDG, OF, EC, SC |
| COMPOUND A | Difenoconazole | Fludioxinil plus Mefenoxam | WDG, OF, EC, SC |
| COMPOUND B | | | WDG, WP |
| COMPOUND C | | | WDG, WP, EC |
| COMPOUND D | | | EC, WP, WDG |

EO = average number of ethylene oxide units

| Code | Description of formulation code |
|---|---|
| DF | dry flowable |
| EC | emulsifiable concentrate |
| EW | water in oil emulsions |
| FL | flowable |
| FS | flowable concentrate for seed treatment |
| GR | granules |
| L | liquid |
| OF | oil miscible flowable concentrate |
| SC | suspension concentrate (suspoemulsion) |
| WDG | wettable dispersible granules |
| WP | wettable powder |
| WS | water dispersible powder for slurry treatment |

TABLE 3

Structures for Compounds A to D:

| | Structure |
|---|---|
| COMPOUND A | 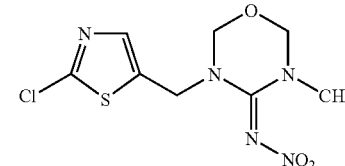 |
| COMPOUND B | 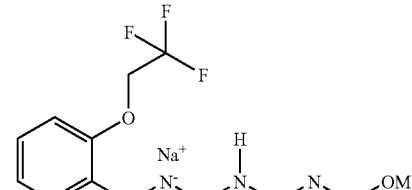 |
| COMPOUND C | 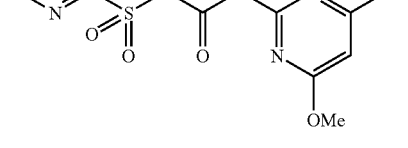 |

TABLE 3-continued

Structures for Compounds A to D:

| | Structure |
|---|---|
| COMPOUND D | 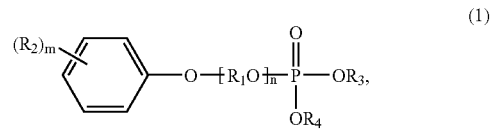 |

Table 4 lists some examples of useful components that may be used to formulate the compositions of the instant invention. However, the invention is not limited to the use of the indicated components in the table. Table 5 provides some sources for commercially available materials. Nevertheless, one of ordinary skill would realized that many of the materials that could be used to practice the instantly disclosed invention may be obtained from any suitable source.

TABLE 4

Examples of components that may be used to formulate the compositions of the instant invention.

| Product Name | Supplier | Description |
|---|---|---|
| Aromatic 150 | Exxon Corporation | aromatic hydrocarbon solvent |
| Pegasol R-150 | Mobil Chemical Company | aromatic hydrocarbon solvent |
| Cyclo Sol 150 | Shelf Chemical Company | aromatic hydrocarbon solvent |
| Pluronic P-65 | BASF Corporation | EO-PO block copolymer |
| Toximul 8323 | Stepan Company | EO-PO block copolymer |
| Antifoam A | Dow Corning Corporation | silicone antifoaming agent |
| Y-6067 | Osi Specialties, Inc. | silicone antifoaming agent |
| Proxel GXL | Zeneca Inc. | biostatic |
| Nipacide BIT20 | Nipa Hardwicke, Inc. | biostatic |
| Renex 36 | ICI Surfactants | Tridecyl alcohol (6EO) |
| Rhodasurf BC-610 | Rhodia Inc. | Tridecyl alcohol (6EO) |
| Genopol X-060 | Clariant Corporation formerly Hoechst Celanese Corporation | Tridecyl alcohol (6EO) |
| Witconol TD-60 | Witco Corporation | Tridecyl alcohol (6EO) |
| Rhodopol 23 | Rhodia Inc. | Xanthan gum |
| Kelzan | Zeneca Inc. | Xanthan gum |

TABLE 5

Names and address of suppliers of materials.

| Supplier | Address |
|---|---|
| Witco Corporation | 5777 Frantz Road, P.O. Box 646, Dublin, Ohio 43017 |
| Stepan Company | Northfield, Illinois 60093 |
| Dow Corning Corporation | Midland, MI 48686 |
| Zeneca Inc. | Wilmington, DE 19897 |
| BASF, Corporation | Mt. Olive, NJ 07828 |
| Rhodia, Inc. | Cranbury, NJ 08512 |
| Nipa Hardwicke, Inc. | 3411 Silverside Road, 104 Hagley Bldg., Wilmington, DE 19810 |
| Osi Specialities, Inc. | Greenwich, CT 06831 |
| ICI Surfactants | Wilmington, DE 19850 |
| Clariant Corporation | Charlotte, NC 28201 |
| Shell Chemical Company | Houston, TX 77251 |
| Exxon Corporation | Houston, TX 77001 |
| Mobil Chemical Company | Houston, TX 77032 |

In summary, it is seen that this invention provides new salt compounds useful as surfactants. In particular, the surfactants of the instant invention are useful for formulating agrochemical compositions. Variations may be made in proportions, procedures and materials without departing from the scope of the invention as defined by the following claims.

What is claimed is:

1. A surfactant system comprising:
   a) at least one alkoxylated polyarylphenol phosphate ester of the formula (1):

$$\text{(1)}$$

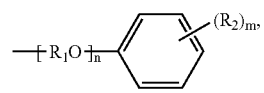

wherein $R_1$ independently is a straight chain or branched $C_2$–$C_4$ alkylene, $R_2$ is phenyl, aryl or alkylaryl, wherein the phenyl nucleus in $R_2$ is unsubstituted or substituted by one to three groups selected from the group consisting of $C_1$–$C_4$ alkyl or $C_1$–$C_4$ alkoxy, and $R_3$ and $R_4$ are independently selected from the group consisting of hydrogen, sodium, potassium, and $$-\!\!-\!\!\text{[}R_1O\text{]}_n\!\!-\!\!\text{(phenyl)}(R_2)_{m'},$$

m, is 2 or 3, and n is a number from 1 to 150 inclusive, and b) at least one alkoxylated lignosulfonate salt.

2. A surfactant system of claim 1, wherein component (a) is the phosphate ester having the formula:

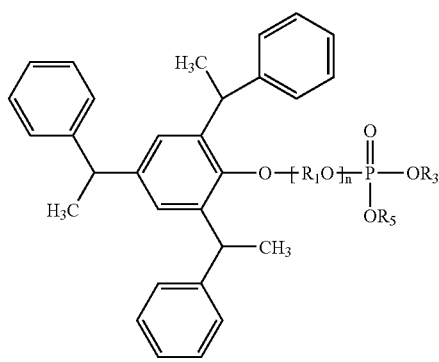

wherein $R_1$ and n are defined as above, and $R_3$ and $R_5$ are independently selected from the group consisting of hydrogen, sodium, potassium, and

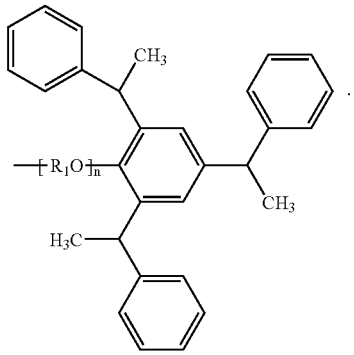

3. A surfactant system of claim 1, wherein component (a) is the phosphate ester having the formula:

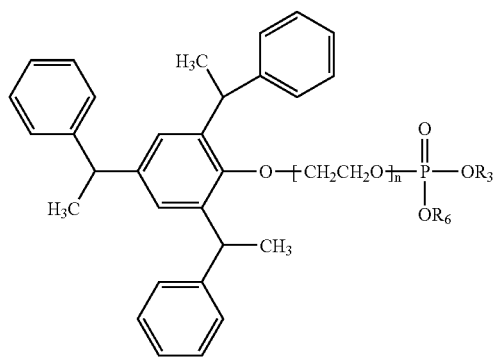

wherein n is defined as above, and $R_3$ and $R_6$ are independently selected from the group consisting of hydrogen, sodium, potassium, and

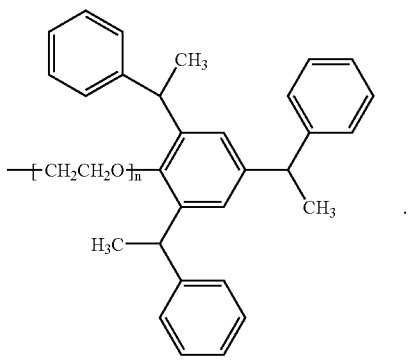

4. A surfactant system according to claim 3, wherein n is 4 to 25.

5. A surfactant system according to claim 3, wherein n is 16.

6. A surfactant system according to claim 3, wherein component (b) is an alkoxylated sulfonated kraft lignin.

7. A surfactant system according to claim 4, wherein component (b) is an ethoxylated sulfonated kraft lignin.

8. A surfactant system according to claim 7, wherein component (b) is the sodium salt of an ethoxylated sulfonated kraft lignin having an EO equal to 2 to 4.

9. A surfactant system according to claim 8, wherein component (b) is the sodium salt of an ethoxylated sulfonated kraft lignin having an EO equal to 3.

10. A surfactant system according to claim 8, wherein component (a) n is 16.

11. A surfactant system according to claim 1, wherein component (a) n is 16 and component (b) has an EO equal to 2 to 4.

12. A pesticide formulation comprising at least one pesticide and
 a) at least one alkoxylated polyarylphenol phosphate ester of the formula (1):

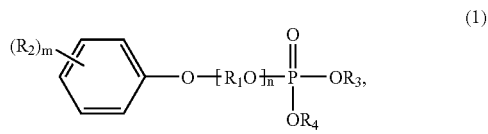

wherein $R_1$ independently is a straight chain or branched $C_2$–$C_4$ alkylene, $R_2$ is phenyl, aryl or alkylaryl, wherein the phenyl nucleus in $R_2$ is unsubstituted or substituted by one to three groups selected from the group consisting of $C_1$–$C_4$ alkyl or $C_1$–$C_4$ alkoxy, and $R_3$ and $R_4$ are independently selected from the group consisting of hydrogen, sodium, potassium, and

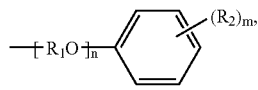

m, is 2 or 3, and n is a number from 1 to 150 inclusive, and
 b) at least one alkoxylated lignosulfonate salt.

13. A pesticide formulation of claim 12 wherein the pesticide is compound A having the formula:

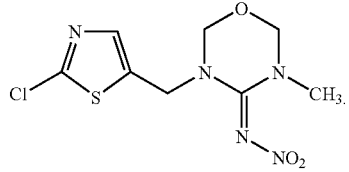

14. A method of protecting crops comprising the step of applying to the locus of the crops in need of protection an agriculturally effective amount of the formulation of claim 12.

15. A method of protecting crops comprising the step of applying to the locus of the crops in need of protection an agriculturally effective amount of the formulation of claim 13.

* * * * *